United States Patent
Rickauer

(10) Patent No.: US 9,277,801 B2
(45) Date of Patent: Mar. 8, 2016

(54) CLEAVAGE PAD

(71) Applicant: Evelyn Rickauer, Bernau (DE)

(72) Inventor: Evelyn Rickauer, Bernau (DE)

(73) Assignee: Evelyn Rickauer, Bernau (DE)

( * ) Notice: Subject to any disclaimer, the term of this patent is extended or adjusted under 35 U.S.C. 154(b) by 0 days.

(21) Appl. No.: 14/831,391

(22) Filed: Aug. 20, 2015

(65) Prior Publication Data

US 2015/0351520 A1 Dec. 10, 2015

Related U.S. Application Data

(62) Division of application No. 14/411,544, filed as application No. PCT/EP2013/056955 on Apr. 2, 2013, now abandoned.

(51) Int. Cl.
| | |
|---|---|
| *A41C 3/00* | (2006.01) |
| *A45D 44/00* | (2006.01) |
| *A41C 3/14* | (2006.01) |
| *A45D 44/22* | (2006.01) |
| *A61F 13/00* | (2006.01) |

(52) U.S. Cl.
CPC ............. *A45D 44/00* (2013.01); *A41C 3/144* (2013.01); *A45D 44/22* (2013.01); *A61F 2013/00374* (2013.01)

(58) Field of Classification Search
CPC ................................. A41C 3/00; A41C 3/0064
USPC .............. 450/81, 54–57, 39, 37; 604/385.01; 623/7, 8
See application file for complete search history.

(56) References Cited

U.S. PATENT DOCUMENTS

| | | | | |
|---|---|---|---|---|
| 1,783,512 A | * | 12/1930 | Mather | A41C 3/065 450/81 |
| 2,001,862 A | * | 5/1935 | Battey | A45D 44/22 604/307 |
| 2,728,079 A | * | 12/1955 | Williams | A41C 3/065 450/53 |
| 2,869,553 A | * | 1/1959 | Or | A41C 3/065 450/81 |
| 3,276,449 A | * | 10/1966 | Burton | A41C 3/065 450/81 |
| 3,280,818 A | * | 10/1966 | Pankey | A41C 3/065 450/81 |
| 3,297,036 A | * | 1/1967 | Williams | A41C 3/065 450/81 |
| 5,961,986 A | * | 10/1999 | Killen | A61F 13/023 424/400 |
| 6,666,747 B1 | * | 12/2003 | Buntz | A41C 3/065 424/400 |
| 2004/0138694 A1 | * | 7/2004 | Tran | A61F 2/01 606/200 |
| 2005/0186885 A1 | * | 8/2005 | Valentin | A41C 3/065 450/81 |
| 2008/0280534 A1 | * | 11/2008 | Chandler | A45D 44/22 450/59 |

* cited by examiner

*Primary Examiner* — Gloria Hale
(74) *Attorney, Agent, or Firm* — Scott R. Cox

(57) ABSTRACT

A cleavage pad for adhering to the skin wherein the outer contour of the cleavage pad is formed by a substantially concave contour and a substantially convex contour having rounded portions in the transitions of both contours, wherein a point of intersection A of the convex contour is provided with an axis of symmetry and a point of intersection B of the concave contour is provided with the axis of symmetry, and wherein a perpendicular projection of the point of the rounded portions of the largest spaced interval from the point of intersection A to the axis of symmetry produces a point C and the ratio of the distance AB/AC is less than 0.8.

15 Claims, 3 Drawing Sheets

CLEAVAGE PAD

CROSS-REFERENCE TO RELATED APPLICATIONS

This application is a divisional application based on application Ser. No. 14/411,544, filed on Dec. 29, 2014.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION (1) Field of the Invention

The invention relates to a cleavage pad for adhering to the skin and a use of a cleavage pad.

(2) Description of Related Art

Pads or adhesive tapes for adhering to the human skin, hence for doing something against the formation of wrinkles are generally known. From U.S. Pat. No. 5,961,986 an adhesive pad which is adhered to the chest of the person for reducing wrinkles is known. In WO 2005/018351 A2 an anti-wrinkle brassiere for use during sleep is disclosed. US 2008/0280534 A1 shows a device which has to be put between the breasts for avoiding wrinkles in the chest region and from CA 2,575,534 a potentially adhesive pad for forming the chest is known. Here the cleavage pads are adhered to the regions in which the formation of wrinkles can occur or has already occurred.

The cleavage pads are based on the knowledge that wrinkles in the décolleté region are caused or at least facilitated through a compression of the skin over a longer period of time, such as e.g. during the sleep on one side. Here and also below, the compression of the skin means a compression of the skin in the plane of the skin surface. This problem is particularly important in the case of the female décolleté.

In the region between the breasts and the region being directly above that generally can be found a particularly strong formation of wrinkles. This is caused or intensified by the fact that during sleep in the case of lying on the side the lower breast is not moved downwards, because it lies on the lower arm or the mattress or optionally it is even moved upwards a little bit due to the lower arm, whereas the upper shoulder and the upper breast are moved downwards due to gravitation. In the middle region of the décolleté thus in a region with nearly equal distances to the breast nipples and the collar bones in a vertical view a nearly uniform distribution of the wrinkles can be found.

The cleavage pads known have a shape which has been optimized with the intention that all sites at which the formation of wrinkles can occur are covered by the pad. Since the stiffness of the known pads is so high that in the case that the person lies on the side a compression of the pad itself does virtually not occur or only in a negligible extent and the skin lying beneath is adhered to the pad, due to the pad no compression of the adhered skin occurs and this counteracts the formation of wrinkles. But this stiffness of the known pads results in a wearing comfort of the person which may partially be unpleasant. One reason for the unpleasant wearing comfort may be that pads known from prior art comprise an extension which is located in the region directly between the breasts, because there the formation of wrinkles may be considerably more distinct. When lying on the side, the upper breast may lie on the rim of this extension of the pad which is oriented upwards and this may cause an unpleasant feeling due to the increased sensitivity of the breast.

BRIEF SUMMARY OF THE INVENTION

The object of the present invention is to improve known cleavage pads in their anti-wrinkle effect and at the same time to achieve a wearing comfort being as pleasant as possible for the wearer. This object is solved by the features of the independent patent claims. Advantageous embodiments can be followed from the dependent patent claims.

DETAILED DESCRIPTION OF THE INVENTION

Figure 1:
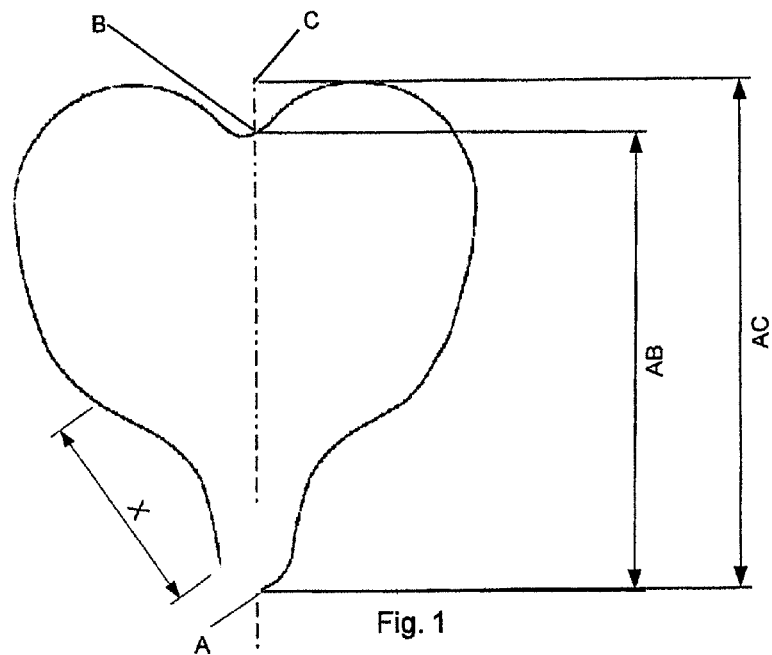
FIG. 1 shows a cleavage pad according to prior art.

A cleavage pad can be adhered to the skin and comprises a backing layer and an adhesive layer, wherein the cleavage pad shows mirror-symmetry to an axis of symmetry. And here the outer contour of the cleavage pad is formed by a substantially concave contour and a substantially convex contour having rounded portions in the transitions of both contours, wherein there a point of intersection A of the convex contour is provided with the axis of symmetry and a point of intersection B of the concave contour is provided with the axis of symmetry and there results a point C from a perpendicular projection of the point of the rounded portions of the largest spaced interval from the point of intersection A to the axis of symmetry. The ratio of the distance AB/AC is less than 0.8 and is preferably 0.6. With this ratio the cleavage pad comprises a kind of neckline. In other words, preferably the above ratio can be described such that the pad on both sides ends near the collar bones. So it is achieved that a total shape results which covers a main part of the upper décolleté. In the taped region a considerably increased stiffness of the décolleté against compression is achieved. Since the taped region covers a relatively large area it is also effected that the whole décolleté and not only the taped regions are protected against compression and a corresponding formation of wrinkles. So it is not necessary to tape the region between the breasts. Because in the case of known embodiments especially here the reason for an unpleasant wearing comfort was found, the wearing comfort is increased.

In particular, the concave contour describes a first circular arc with a tolerance of +/−2 cm, wherein in particular the radius of the first circular arc is 9.5 cm. According to a preferable embodiment the radius of the first circular arc is 9 cm. With the concave circular arc contour so the pad can be applied with a constant distance to the neck. Here the ends of the upper sections of the pad are located very near below the collar bones.

Furthermore, the convex contour describes a second circular arc with a tolerance of +/−3 cm and preferably it describes the second circular arc with the tolerance of +/−2.5 cm, in particular with the tolerance of +/−2 cm, wherein in particular the radius of the second circular arc is 11 cm. According to a preferable embodiment the radius of the second circular arc is 10 cm. This means that the pad has a design with a substantially crescentic shape and is substantially applied in the décolleté region above the breasts and to a lesser extent in the region between the breasts.

A point A of the convex contour is on the axis of symmetry of the cleavage pad and the convex contour describes a second circular arc with a tolerance of +/−3 cm. Here the convex contour within an arc angle range of the convex contour with respect to the center of the second circular arc of +/−35°, in particular +/−30° around the point of intersection A consists of radiuses which are higher than the radius of the second circular arc. In particular, the maximum difference of the radiuses from the radius of the second circular arc is 2 cm or lower. This is a systematic difference with respect to prior art. Up to now embodiments of the pad with a relatively sharp extension tapering off into the region between the breasts were known. But here the radius is more flattened which results in the already discussed advantages.

Furthermore, the outer contour of the cleavage pad may comprise a substantially convex contour, wherein a point of intersection of the convex contour is provided with the axis of symmetry of the cleavage pad and the radius of a second circular arc is at least 8 cm, in particular at least 9 cm and the convex contour within an circular angle range of +/−35° around the point of intersection is within a tolerance range of +/−1 cm with respect to the second circular arc. Accordingly this description means that the cleavage pad above the region between the breasts is flattened and does not comprise an extension tapering off into the region between the breasts.

In particular, the size of the cleavage pad is such that the cleavage pad can comprise a rectangular area being arranged perpendicularly with respect to the axis of symmetry with dimensions of at least 14.5 cm*3.5 cm. According to a preferable embodiment the size of the cleavage pad is such that the cleavage pad can comprise a rectangular area being arranged perpendicularly with respect to the axis of symmetry with dimensions of at least 15 cm*4 cm. The pads of prior art have a targeted design of taping virtually exclusively the region in which the most wrinkles occur, thus in particular a wedge-shaped form in the region between the breasts. However it has been understood that a horizontally adhered tape with the mentioned dimensions can stabilize the skin of the whole décolleté in such a manner that therewith also adjacent skin regions which are not taped are protected from the formation of wrinkles. The cleavage pad is larger than the mentioned dimensions for further supporting the effect.

Advantageously the cleavage pad comprises a circumferential edge with a width of 2 mm+/−1 mm, wherein there the thickness of the cleavage pad is reduced in a distinct extent with respect to the remainder of the cleavage pad. Thus an outer region with lower strength results for reducing or avoiding pressure marks of the rim at the breast.

The cleavage pad may also comprise a circumferential edge with a width of 2 mm+/−1.5 mm, wherein there the thickness of the cleavage pad is reduced in an extent of at least % with respect to the remainder of the cleavage pad, by which also an edge region with lower strength results for reducing pressure marks. The edge may be so thin and/or so flexible that it can be bended with respect to the pad and that the breast can be in contact with the bended region, by which via an increase of the contact area an optionally unpleasant feeling can further be reduced.

The pad can also be provided with an outer circumferential edge which does not comprise any adhesive coating, by which the removal of the separation layer from the pad becomes easier.

Preferably, the maximum width of the cleavage pad in the direction perpendicularly to the axis of symmetry is at least 18 cm, whereby a main part of the upper décolleté is covered. With the dimensions of the cleavage pad according to the present invention in a surprisingly favorable manner a stabilization of the skin in the regions of the décolleté which are relevant for the formation of wrinkles becomes possible, wherein at the same time a very good wearing comfort is guaranteed.

According to an embodiment a cleavage pad for adhering to the skin comprises a layer of an adhesive silicone for adhering to the body and an outer layer of a first polyurethane foil, being arranged at the far side with respect to the body during the use of the cleavage pad. Preferably, between the outer layer and the layer of adhesive silicone a second polyurethane foil and a silicone layer are arranged and the silicone layer is arranged between the first and the second polyurethane foils. In this case both polyurethane foils are circumferentially adhered or fused at their external ends.

According to a further embodiment only one plastic foil or even no plastic foil is used for further simplifying the structure. In such a case preferably the backing layer of silicone has a sufficient stability for being capable of functioning as a backing layer in the sense of the invention—as described above. Preferably, the thickness is 1.75 mm and in variant embodiments it is between 1.3 and 3 mm. According to an embodiment the adhesive layer may directly be applied onto the backing layer. According to a preferable embodiment, so the cleavage pad consists of a backing layer and an adhesive layer. Preferably, the backing layer (and preferably also the adhesive layer) has a homogenous structure, i.e. in particular it is not composed of several layers.

According to an embodiment at the circumferential edge the thickness of the silicone layer may be reduced in a successively decreasing manner for obtaining an increased elasticity in this region for thus avoiding pressure marks at the breast. According to an embodiment the minimum thickness of the edge may be between 10-80% of the total thickness. In addition, in an embodiment it may be that the circumferential edge of the backing layer is not provided with the adhesive layer for making it easier to remove the pad from the separation layer or the body. In an alternative embodiment the edge may also be provided with the adhesive layer.

A further aspect according to the present invention relates to the use of the pad according to the present invention as described in the present specification and the patent claims for adhering to the skin in the décolleté region of the chest. A further aspect relates to adhering to the skin and wearing of the cleavage pad on the skin during the night, in particular during the sleep. Preferably, the cleavage pad is used for preventing the formation of wrinkles in the region of the décolleté and/or for doing something against décolleté wrinkles, in particular in the case of persons who sleep on their sides.

With the advantageous stabilization of the skin by means of the adhered cleavage pad the skin does not wrinkle in the regions which are relevant for the prevention of wrinkle formation in such a strong extent, but maximally in an extent of larger soft waves. So the deformation of the skin is minimized such that no pressure wrinkles result. The cleavage pad according to the present invention stabilizes the thin fine skin in the relevant regions of the décolleté quasi in the form of a thicker, more robust skin. Here due to its dimensions and nature the cleavage pad stays so soft and smooth that a high wearing comfort results. Due to the design of the cleavage pad according to the present invention this wearing comfort is also guaranteed in different preferable lying and/or sleeping positions.

Preferably, on the cleavage pad according to the present invention, in particular on its adhesive layer, no non-adhesive pillow is arranged, such as e.g. can be found in the case of adhesive plasters. So preferably one side of the cleavage pad is completely, i.e. with its whole surface, or substantially completely self-adhesive and can so be adhered to the skin for carrying. According to an embodiment an edge region can optionally be free of the adhesive coating, as described above.

Below the invention is described by means of preferable embodiments. The single features described with reference to the figures have to be understood as independent and combinable embodiments, insofar they are not obvious alternatives which are mutually exclusive.

FIG. 1 shows a cleavage pad of prior art. This embodiment has an approximately heart-shaped basic form. The lower tip of the heart is designed such that it reaches into the region between both breasts. At the arms extending from the tip of the heart-shaped contour regions X with a slightly concave form are arranged. When lying on the side, namely the upper breast each lies on the outer contour of the pad and this may cause an unpleasant feeling, pressure marks and pains at the sensitive breast tissue. In prior art with this concave contour X it is tried to reduce this problem.

Figure 2:
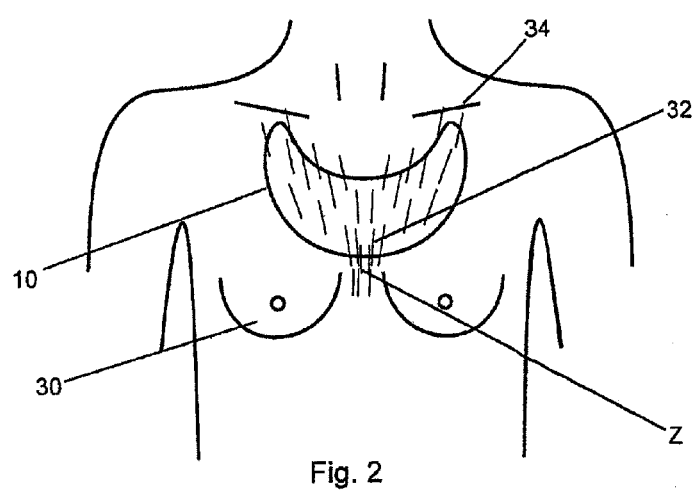
FIG. 2 shows a view of a female upper body with a cleavage pad according to the present invention.

FIG. 2 shows a female upper body with breasts 30 and a cleavage pad 10 being adhered to the décolleté. In addition, wrinkles 32 are shown which often arise at the décolleté of women, when they sleep on their sides. Here the wrinkles in the region between the breasts are more distinct than in the upper region of the décolleté.

Figure 3:
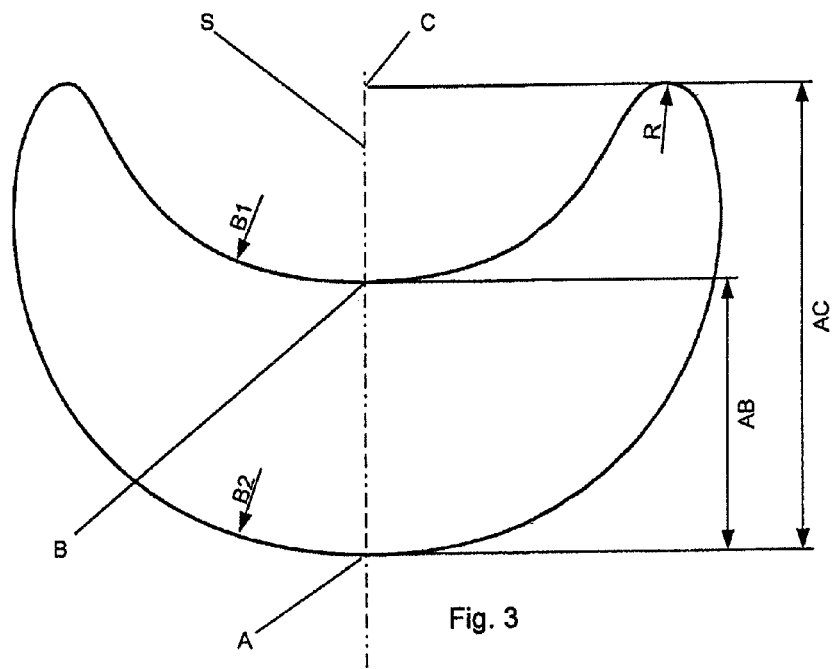
FIG. 3 to FIG. 6 show views of the cleavage pad with different dimensioning and FIG. 7 shows a profile of the cleavage pad.

In FIG. 2 is shown that on the décolleté a cleavage pad 10 is adhered and in FIG. 3 this one is shown in an enlarged view. In horizontal direction which means the alignment in the case of the use with a standing person the width of the cleavage pad is 24 cm. The cleavage pad 10 has a crescent or half-moon shape consisting substantially of both arcs B1 and B2 which at the transitions to each other are provided with a radius R. For the purpose of explanation on the cleavage pad 10 the axis of symmetry S and the points of reference A to C are defined. The axis of symmetry S is the vertical axis which separates the cleavage pad into two identical parts with mirror-symmetry. The point of intersection of the axis of symmetry S with the convex arc B2 is referred to as A. The point of intersection of the concave arc B1 with the axis of symmetry S is referred to as B. Furthermore, a point C is defined as the point resulting from a perpendicular projection of the highest point of the cleavage pad to the axis of symmetry. In an alternative this point C can be referred to as the point resulting from the projection of the point of the cleavage pad of the largest spaced interval from the point A to the axis of symmetry.

The height of the cleavage pad, thus the distance between the points A and C is 15.5 cm. Here the crescent of the pad is formed via two arcs B1 and B2 which are substantially circular arcs comprising in the transition to each other a rounded portion R. The radius of the rounded portion is preferably between 10 and 20 mm. The arc B1 describes the smaller inlying and concave arc and has approximately the form of a circular arc with the radius 9.5 cm. Here the exact radius form is not essential, but in a preferable embodiment the contour of the arc B1 describes this arc with a deviation of +/−15 mm, preferably +/−5 mm. During the use of the cleavage pad the arc B1 is equidistant to the neck of the wearer. Here the ends of the crescent form of the cleavage pad, thus the region of the radiuses R are below the collar bones of the wearer and are arranged in a distance to the collar bones of ca. 3 cm. So it is achieved that below the collar bones no formation of wrinkles can occur or there the formation of wrinkles is at least reduced. The width of the tolerance area of arc B1 is shown in FIG. 4 with T1 and this defines the deviation of arc B1 with respect to the ideal circular arc form K1 which can occur in embodiments according to the present invention.

Arc B2 describes the larger external and convex arc and has the form of an approximately circular arc with a radius K2 (see FIG. 5) of 11.3 cm with a tolerance range T2. Here arc B2 in a preferable embodiment has a deviation from the circular arc form with the radius K2 of not more than +/−15 mm (preferably +/−10 mm).

In FIG. 2 can be seen that the cleavage pad does not extend into the region Z between the breasts. When considering the geometry it becomes obvious that with the distance AB the neckline is larger than in known embodiments. Generally this results in the fact that the ratio of the distances AB/AC is less than 0.8. This ratio results in covering of a relatively large area in the upper chest region. Due to the stiffness of the pad it is achieved that in the case of lying on the side the whole skin in the upper chest region can drop down only in a considerably lower extent than in the case of known embodiments. With this area distribution and the thus attained increase of the stiffness of the upper chest it is achieved that it is not possible to compress the skin in the region between the breasts Z, and so in this region Z something is done against the formation of wrinkles, without adhering a section of the pad in this region.

Figures 4, 5:
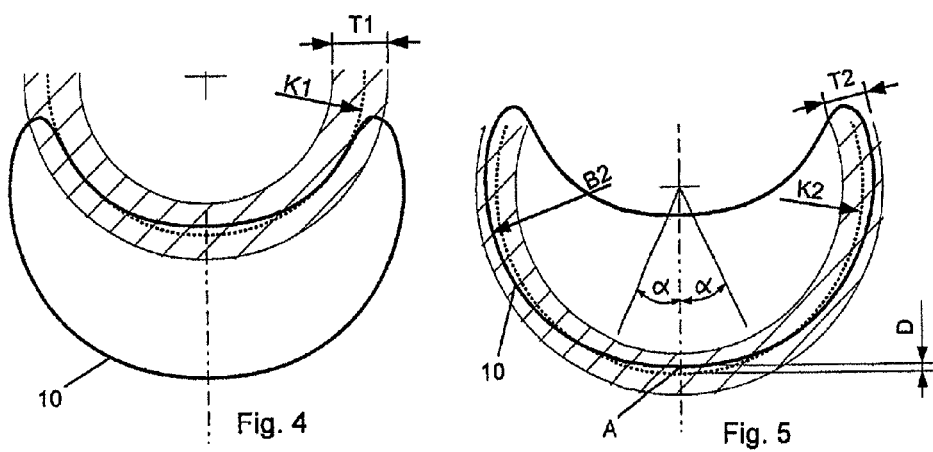

In FIG. 5 can be seen that arc B2 in the vicinity of point A has a higher radius than the radius of the circular arc K2. So at point A a distance D between the circular arc K2 and the arc B2 results. So the outer contour of the cleavage pad above the region between the breasts Z is more flattened in comparison with the ideal circular arc form K2. Accordingly, the region between the breasts Z is not covered by the cleavage pad and the total stiffness of the pad has the effect that the skin in the region between the breasts cannot be compressed and so also without adhering the pad in the region between the breasts Z it is prevented that here the skin can form wrinkles, when lying on the side.

Figure 6:
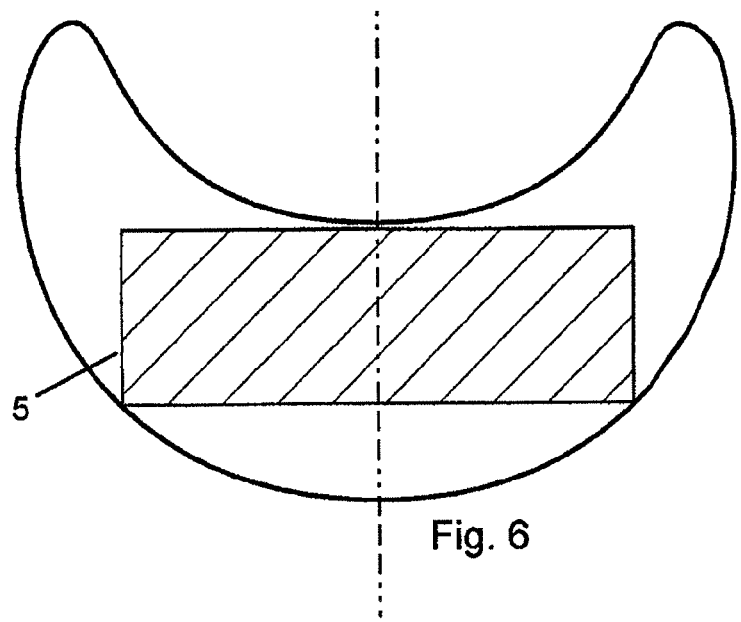

FIG. 6 in addition supports the understanding of the schematic structure of the pad. The area of the pad is of such size that in it a rectangle with the dimensions of 19.5 cm*5 cm is contained. This rectangle is a strip above the breasts and results in the effect that the skin in the region above the breasts cannot be compressed. The residual regions of the pad support this effect.

Figure 7:
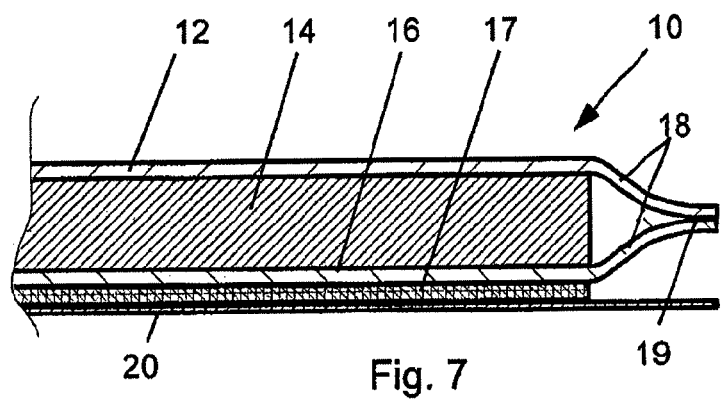

In FIG. 7 the structural constitution of the cleavage pad 10 can be seen. A silicone layer 14 is placed between an outer first plastic foil 12 and a lower second plastic foil 16 so that a sandwich structure results. Both plastic foils 12 and 16 preferably have the same thickness of 10 μm to 200 μm and preferably a thickness of 100 μm+/−30 μm and they are manufactured from a thermoplastic material such as for example polyurethane. The silicone layer 14 lying in between has a maximum layer thickness of 5 mm and preferably a layer thickness of 1.5 mm+/−1 mm. The strength of the silicone layer is 5 Shore 00-65 Shore 00. This sandwich structure on the one hand results in the fact that both plastic foils 12 and 16 are spaced at a certain distance from one another which increases the strength of the pad against side-on compression. But on the other hand the bending property of the cleavage pad is retained so that the cleavage pad itself being adhered to the chest can conform to the body contour.

For adhering the cleavage pad to the skin on the outer side of the second plastic foil an adhesive layer 17 of an adhesive silicone with a thickness of 0.2 mm is applied, wherein in an alternative the thickness may have a value of up to 5 mm.

The silicone layer 14 is a layer being punched from a foil so that it comprises cutting rims and thus end faces which are arranged in a perpendicular manner with respect to the foil. The size of the plastic foils 12 and 16 exceeds that of the silicone layer 14 by 2 mm so that a circumferential edge 18 is formed. At the external end 19 of the edge 18 the plastic foils 12 and 16 are fused with one another. The size of the adhesive layer 17 more or less corresponds to the size of the silicone layer 14. Since in the edge region 18 between the foils 12 and 16 no silicone is contained, it is considerably softer than the remainder of the cleavage pad. When the wearer lies on the side, the breasts may be pressed against edge 18. Then the edge is deformed and this results in a larger contact area with the breast so that an unpleasant feeling is avoided.

At the lower side of the adhesive layer 17 a separation layer 20 of a thinner plastic foil or wax paper is arranged which can easily be removed from the adhesive layer 17. Since the separation layer at the edge 18 is not connected with the cleavage pad, it can easily be removed by the user, and subsequently the cleavage pad with the adhesive layer 17 is adhered to the décolleté.

Figure 8:
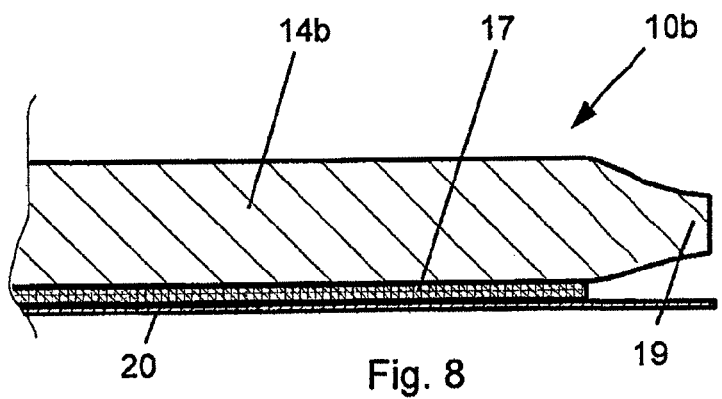
FIG. 8 shows a profile of a variant cleavage pad.

FIG. 8 shows a variant of the cleavage pad having a modified structure. Here no plastic foils 12, 16 are used. Instead, the silicone layer 14b has sufficient stability so that it can serve as a backing layer—as described above. Preferably, the thickness is 1.75 mm and in the case of variants it is between 1.5 and 3 mm. At the circumferential edge 18 with the width of 2 mm the thickness of the silicone layer is reduced in a successively decreasing manner for obtaining an increased elasticity in this region to avoid pressure marks at the breast. The minimum thickness of the edge is between 40-80% of the total thickness. In addition, optionally it is possible that the circumferential edge 18 is provided without any adhesive layer 17 for facilitating the removal of the pad from the separation layer 20. In an alternative embodiment also the edge 18 may be provided with the adhesive layer. Advantageously, in this case the separation layer 20 protrudes beyond the edge 18 (not shown in FIG. 8) so that the separation layer can be grasped very easily, when it is removed from the pad.

When the figures have been drawn care has been taken on the proportionality of the figures so that further preferable size and/or angle ratios of the figures which are not explicitly mentioned in the description can be learned from them.

The invention claimed is:

1. A process for reducing formation of wrinkles in the region of the décolleté comprising
    adhering a décolleté pad to skin above breasts in the décolleté region of a human chest,
    wherein the décolleté pad comprises a backing layer and an adhesive layer, wherein the décolleté pad shows mirror-symmetry along a symmetry axis, wherein an overall contour of the décolleté pad exhibits a concave contour on one side and a convex contour on another side with curvatures in the areas of contact of the skin of both contours, characterized in that there is a first point of intersection of the convex contour with the symmetry axis and a second point of intersection of the concave contour with the symmetry axis and where an additional point results from a perpendicular projection of the point of the curvatures with a greatest distance from the first point of intersection on the symmetry axis, and the ratio of a distance between the first point of intersection of the convex contour with the symmetry axis and the second point of intersection of the concave contour with the symmetry axis to a distance between the first point of intersection and the additional point resulting from and the introduction of the perpendicular projection of the point of curvature with the greatest distance from first point of interaction on the symmetry axis is smaller than 0.8.

2. The process according to claim 1, characterized in that the concave contour of the décolleté pad describes a first circular arc with a tolerance of +/−2 cm, wherein a radius of the first circular arc is 9 cm+/−2.5 cm.

3. The décolleté according to claim 1, characterized in that the convex contour of the décolleté pad describes a second circular arc with a tolerance of +/−3 cm, wherein a radius of the second circular arc is 11 cm+/−1 cm.

4. The process according to claim 1, characterized in that the convex contour of the décolleté pad describes a second circular arc with a tolerance of +/−3 cm, wherein a radius of the second circular arc is 10 cm+/−2 cm.

5. The process according to claim 3 wherein the radius of the second circular arc of the décolleté pad is at least 8 cm, and the convex contour has an angle range of a circular arc of +/−35° around a point of intersection, wherein the tolerance range is +/−1 cm with respect to the second circular arc.

6. The process according to claim 1 wherein the décolleté pad further comprises a rectangular area arranged perpendicularly on the pad with respect to the symmetry axis with dimensions of about 14.5 cm*3.5 cm.

7. The process according to claim 1 wherein the décolleté pad further comprises a circumferential edge with a width of 2 mm+/−1 mm, wherein a thickness of the circumferential edge is reduced at least 20% in comparison with a thickness of a remainder of the décolleté pad.

8. The process according to claim 1 wherein the décolleté pad further comprises a circumferential edge with a width of 2 mm+/−1.5 mm, wherein a thickness of the circumferential edge is reduced at least 60% with respect to a thickness of a remainder of the décolleté pad.

9. The process according to claim 7, characterized in that at the circumferential edge of the décolleté pad comprises no adhesive coating.

10. The process according to claim 1, characterized in that a maximum width of the décolleté pad arranged in a direction perpendicularly to the symmetry axis is 18 cm.

11. The process according to claim 1 wherein one or preferably both of the backing and adhesive layers of the décolleté pad are homogenously designed.

12. The process according to claim 1 wherein the adhesive layer of the décolleté pad comprises a layer of an adhesive silicone for adhering to the body and where the décolleté pad further comprises an outer layer of a first plastic foil arranged at a far side with respect to the chest during use of the décolleté pad.

13. The process according to claim 12, characterized in that between the outer layer and the layer of adhesive silicone of the décolleté pad is a second plastic foil, and a silicone layer, wherein the silicone layer is arranged between the first and the second plastic foils.

14. The process according to claim 13, characterized in that both plastic foils of the décolleté pad are circumferentially adhered or fused at their external ends.

15. The process according to claim 8, characterized in that at the circumferential edge of the décolleté pad comprises no adhesive coating.

* * * * *